United States Patent
Gohno et al.

(10) Patent No.: US 7,164,746 B2
(45) Date of Patent: Jan. 16, 2007

(54) X-RAY CT APPARATUS AND IMAGING METHOD

(75) Inventors: Makoto Gohno, Tokyo (JP); Masatake Nukui, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 3 days.

(21) Appl. No.: 11/032,559

(22) Filed: Jan. 10, 2005

(65) Prior Publication Data

US 2005/0157840 A1 Jul. 21, 2005

(30) Foreign Application Priority Data

Jan. 20, 2004 (JP) ............................. 2004-011594

(51) Int. Cl.
*A61B 6/03* (2006.01)
(52) U.S. Cl. .............................. 378/4; 378/15; 378/901
(58) Field of Classification Search .................... 378/4, 378/15, 901, 62
See application file for complete search history.

(56) References Cited

U.S. PATENT DOCUMENTS

| | | | |
|---|---|---|---|
| 5,090,037 A | 2/1992 | Toth et al. ...................... 378/4 |
| 5,377,250 A | 12/1994 | Hu ................................ 378/15 |
| 5,404,293 A | 4/1995 | Weng et al. .................... 378/15 |
| 5,625,660 A | 4/1997 | Tuy .............................. 378/15 |
| 5,740,224 A | 4/1998 | Muller ......................... 378/11 |
| 6,091,846 A | 7/2000 | Lin et al. ..................... 382/145 |
| 6,243,436 B1 * | 6/2001 | Hahn et al. ..................... 378/4 |
| 6,246,787 B1 | 6/2001 | Hennessey et al. .......... 382/141 |
| 6,483,938 B1 | 11/2002 | Hennessey et al. .......... 382/149 |
| 6,973,158 B1 | 12/2005 | Besson ......................... 378/16 |

FOREIGN PATENT DOCUMENTS

| | | |
|---|---|---|
| JP | 10-052423 A | 2/1998 |
| JP | 2002-177262 A | 6/2002 |
| JP | 2002-336239 | 11/2002 |
| JP | 2004-008398 A | 1/2004 |

OTHER PUBLICATIONS

An English translation of JP 10-052423A.
An English translation of JP 2002-177262 A.
An English translation of JP2004-008398 A.

* cited by examiner

*Primary Examiner*—Courtney Thomas
(74) *Attorney, Agent, or Firm*—Carl B. Horton, Esq.; Armstrong Teasdale LLP (57) ABSTRACT

An imaging method for an X-ray CT apparatus having an X-ray source and an X-ray detector disposed to face the X-ray source with a subject placed therebetween, for rotating at least one of the X-ray source and X-ray detector around the subject and detecting X-rays emitted from the X-ray source toward the subject by the X-ray detector, comprises the steps of: defining a reconstruction plane for the subject in a plane non-parallel to a plane formed by rotation of at least one of the X-ray source and X-ray detector around the subject; scanning the subject by emitting cone-shaped X-rays from the X-ray source; and reconstructing a tomographic image of the subject based on the defined reconstruction plane.

18 Claims, 5 Drawing Sheets

X-RAY CT APPARATUS AND IMAGING METHOD

This application claims the benefit of Japanese Application No. 2004-011594 filed Jan. 20, 2004.

BACKGROUND OF THE INVENTION

The present invention relates to an X-ray CT apparatus and an imaging method, and more particularly to an X-ray CT apparatus and an imaging method for emitting cone-shaped X-rays to scan a subject.

As an apparatus for capturing a tomographic image, there is known, for example, an X-ray CT (computed tomography) apparatus for emitting X-rays as radiation, detecting X-rays passing through a subject, and arithmetically producing a tomographic image.

The X-ray CT apparatus has a scan gantry comprised of an X-ray tube and a detector array disposed to face the X-ray tube with the subject placed therebetween, and detects X-rays emitted toward the subject from the X-ray tube by the X-ray detector array. The X-ray CT apparatus scans the subject while rotating the scan gantry around the subject. Consequently, projection data of the subject are obtained in a plurality of views. The X-ray CT apparatus reconstructs the resulting projection data to produce a tomographic image of the subject of a predetermined slice thickness.

In general, the X-ray CT apparatus conducts reconstruction to produce a tomographic image of a subject in a plane parallel to the direction of rotation of the scan gantry, or a plane parallel to the direction of X-ray emission of a fan beam or the like from an X-ray source. For example, the apparatus produces a tomographic image of a subject in a plane orthogonal to a direction of a body axis from the head to toes, i.e., it produces an axial image.

To produce a tomographic image in a direction different from the direction of rotation or the direction of X-ray emission, an axial image is produced by reconstruction, and thereafter, image processing is applied again to produce a tomographic image in the different direction, for example.

On the other hand, an X-ray CT apparatus having a plurality of X-ray detectors two-dimensionally arranged is known. Since a set of the plurality of X-ray detectors is arranged to have a width in a direction along a certain axis with respect to a subject, it is called a multi-row X-ray detector array.

One known technique of reconstructing a tomographic image using the multi-row X-ray detector array is a cone-beam reconstruction technique (see Patent Document 1). For example, as the X-ray source emits cone-shaped X-rays (which will be sometimes referred to as a cone beam), the X-ray CT apparatus rotates the X-ray source and multi-row X-ray detector around a predefined axis to scan a subject. Since a plurality of X-ray detector rows are present in the predefined axis direction, a plural number, corresponding to the number of X-ray detector rows, of tomographic images of the subject can be obtained in one scan.

In the cone beam reconstruction technique, as in the scan using a fan beam, a tomographic image parallel to the direction of rotation or the direction of detector rows is produced by reconstruction.

[Patent Document 1] Japanese Patent Application Laid Open No. 2002-336239.

SUMMARY OF THE INVENTION

Therefore, an object of the present invention is to provide an X-ray CT apparatus and an imaging method that can easily produce an arbitrary tomographic image of a subject without depending upon the direction of X-ray To attain the aforementioned object, an X-ray CT apparatus of the present invention has an X-ray source and an X-ray detector disposed to face the X-ray source with a subject placed therebetween, for rotating at least one of the X-ray source and X-ray detector around the subject and detecting X-rays emitted from the X-ray source toward the subject by the X-ray detector, and comprises: defining means for defining a reconstruction plane for the subject in a plane non-parallel to a plane formed by rotation of at least one of the X-ray source and X-ray detector around the subject.

According to the X-ray CT apparatus of the present invention, a reconstruction plane is defined beforehand in an arbitrary three-dimensional direction.

To attain the aforementioned object, an imaging method of the present invention is for an X-ray CT apparatus having an X-ray source and an X-ray detector disposed to face the X-ray source with a subject placed therebetween, for rotating at least one of the X-ray source and X-ray detector around the subject and detecting X-rays emitted from the X-ray source toward the subject by the X-ray detector, and comprises the steps of: defining a reconstruction plane for the subject in a plane non-parallel to a plane formed by rotation of at least one of the X-ray source and X-ray detector around the subject; scanning the subject while emitting cone-shaped X-rays from the X-ray source; and reconstructing a tomographic image of the subject based on the defined reconstruction plane.

According to the imaging method of the present invention, a reconstruction plane for the subject is defined in a plane non-parallel to a plane formed by rotation of at least one of the X-ray source and X-ray detector around the subject.

Next, cone-shaped X-rays are emitted from the X-ray source to scan the subject.

Next, a tomographic image of the subject is reconstructed based on the defined reconstruction plane.

According to the X-ray CT apparatus of the present invention, an arbitrary tomographic image of the subject can be easily produced.

According to the imaging method of the present invention, an arbitrary tomographic image of the subject can be easily produced.

Further objects and advantages of the present invention will be apparent from the following description of the preferred embodiments of the invention as illustrated in the accompanying drawings.

DETAILED DESCRIPTION OF THE INVENTION

The best mode for carrying out the present invention will be now described with reference to the accompanying drawings.

Figure 1:
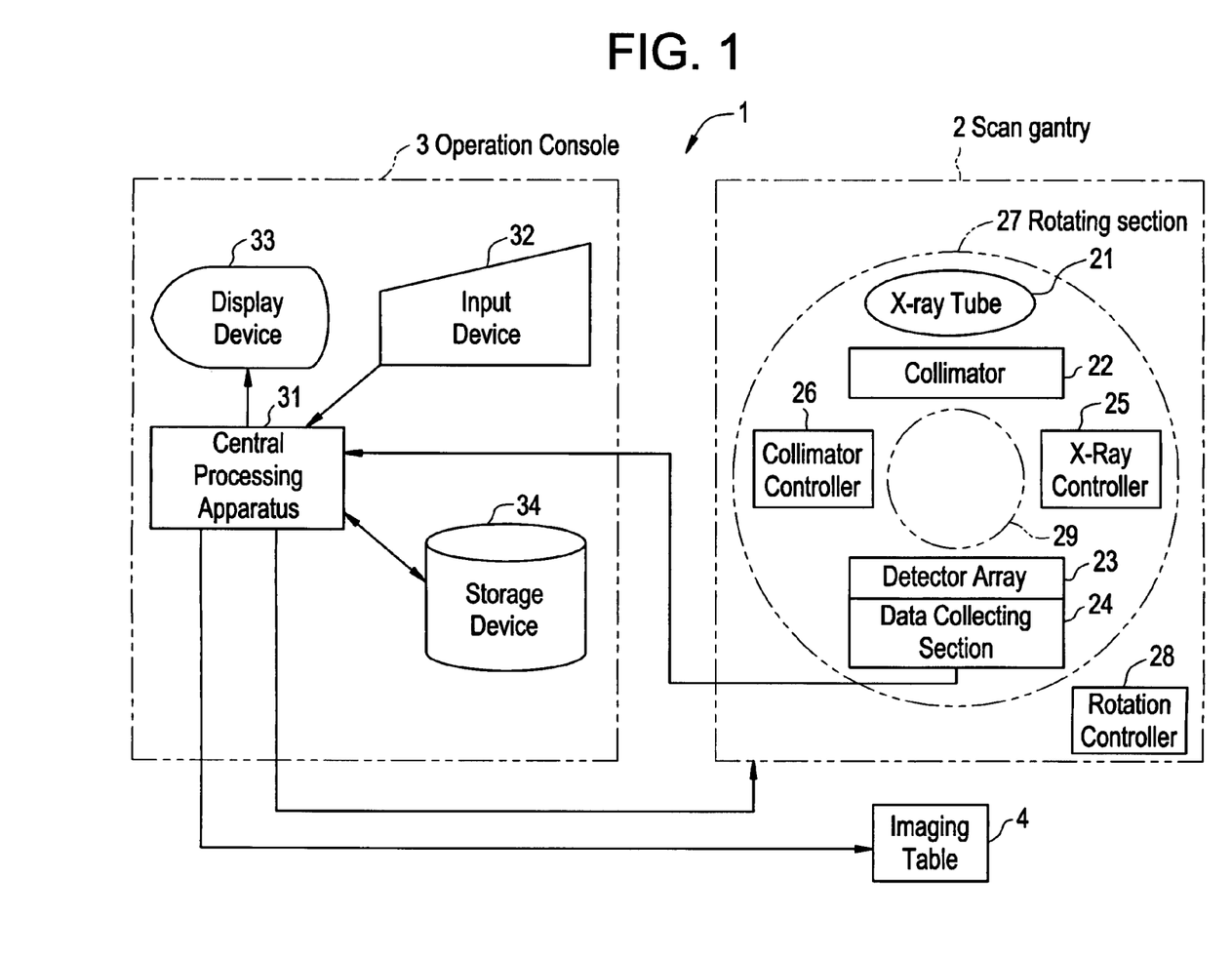
FIG. 1 is a block diagram schematically showing an X-ray CT apparatus 1 in accordance with one embodiment of the present invention.

FIG. 1 is a block diagram showing the overall configuration of an X-ray CT apparatus 1 in accordance with the present invention.

As shown in FIG. 1, the X-ray CT apparatus 1 comprises a scan gantry 2, an operation console 3, and an imaging table (cradle) 4. The imaging table 4 has a subject placed thereon at a certain position.

The scan gantry 2 comprises an X-ray tube 21, a collimator 22, a detector array 23, a data collecting section 24, an X-ray controller 25, and a collimator controller 26.

The X-ray tube 21 emits X-rays. The X-rays emitted by the X-ray tube 21 are shaped into a cone beam by the collimator 22, and cast upon the detector array 23. One embodiment of the X-ray source of the present invention is represented by the X-ray tube 21.

The detector array 23 is, for example, a multi-row detector having a plurality of X-ray detectors elements two-dimensionally arranged. One embodiment of the X-ray detector array of the present invention is represented by the detector array 23.

The detector array 23 generally forms a semicircular-cylindrically concaved X-ray reception surface. The detector array 23 is made of a combination of scintillators and photodiodes, for example. The X-ray detector array 23 is, however, not limited to having such a configuration but may comprise, for example, semiconductor X-ray detector elements employing a cadmium-tellurium (CdTe) or ionization chamber X-ray detector elements employing Xe gas. The detector array 23 is connected to the data collecting section 24.

The data collecting section 24 collects data detected by the individual X-ray detector elements in the detector array 23.

The X-ray controller 25 controls X-ray emission from the X-ray tube 21.

The collimator controller 26 controls the collimator 22.

The interconnection between the X-ray tube 21 and X-ray controller 25, and that between the collimator 22 and collimator controller 26 are omitted in the drawing.

The X-ray tube 21, collimator 22, detector array 23, data collecting section 24, X-ray controller 25 and collimator controller 26 are mounted on a rotating section 27 of the scan gantry 2. The subject is placed on a cradle in a bore 29 in the center of the rotating section 27.

The rotating section 27 rotates under control by a rotation controller 28. The rotating section 27 emits X-rays at the X-ray tube 21, and detects X-rays passing through the subject at the detector array 23 as projection information for each view. The interconnection between the rotating section 27 and rotation controller 28 is omitted in the drawing.

The operation console 3 comprises a central processing apparatus 31, an input device 32, a display device 33, and a storage device 34.

The central processing apparatus 31 is comprised of a microprocessor and a memory, for example. The central processing apparatus 31 controls the operation of the scan gantry 2 in accordance with a program stored in the storage device 34. The central processing apparatus 31 also has at least a function of collecting projection data obtained by detecting X-rays passing through the subject at the detector array 23, and a function of reconstructing a tomographic image of the subject based on the collected X-ray projection data.

Image reconstruction processing by the central processing apparatus 31 will be discussed later.

The central processing apparatus 31 is connected with the display device 33 and input device 32.

The display device 33 displays tomographic image information and the like output from the central processing apparatus 31.

The input device 32 is operated by a user, and supplies several kinds of commands and information to the central processing apparatus 31.

The user uses the display device 33 and input device 32 to interactively operate the present apparatus.

Figure 2:
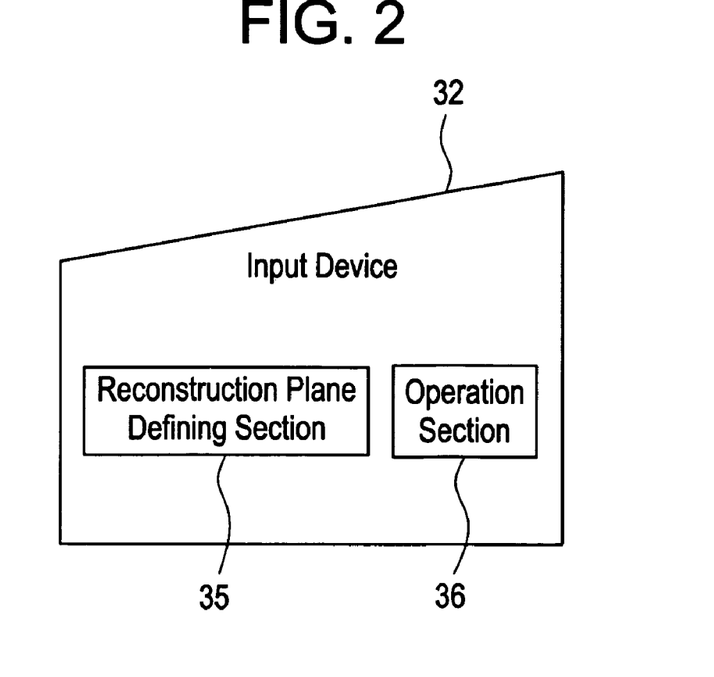
FIG. 2 is a block diagram schematically showing the input device 33 in the X-ray CT apparatus 1 shown in FIG. 1.

FIG. 2 is a block diagram schematically showing an exemplary configuration of the input device 32.

The input device 32 comprises a reconstruction plane defining section 35, and an operating section 36. The input device 32 is operated by the user, and outputs input information to the central processing apparatus 31.

The reconstruction plane defining section 35 is comprised of, for example, a trackball and a keyboard. The reconstruction plane defining section 35 selects a reconstruction plane by moving a cursor displayed on the display device 33 using the trackball or the like, and defines the reconstruction plane by an operation by the user. Moreover, the reconstruction plane defining section 35 sets an interval at which reconstruction planes are produced, by a keyboard operation by the user, for example. One embodiment of the means for defining a reconstruction plane of the present invention is represented by the reconstruction plane defining section 35.

The operating section 36 is comprised of, for example, a keyboard. The operating section 36 is for setting parameters other than the definition of the reconstruction plane. The trackball, keyboard etc. comprising the reconstruction plane defining section 35 and operating section 36 may be shared between them.

Figure 3:
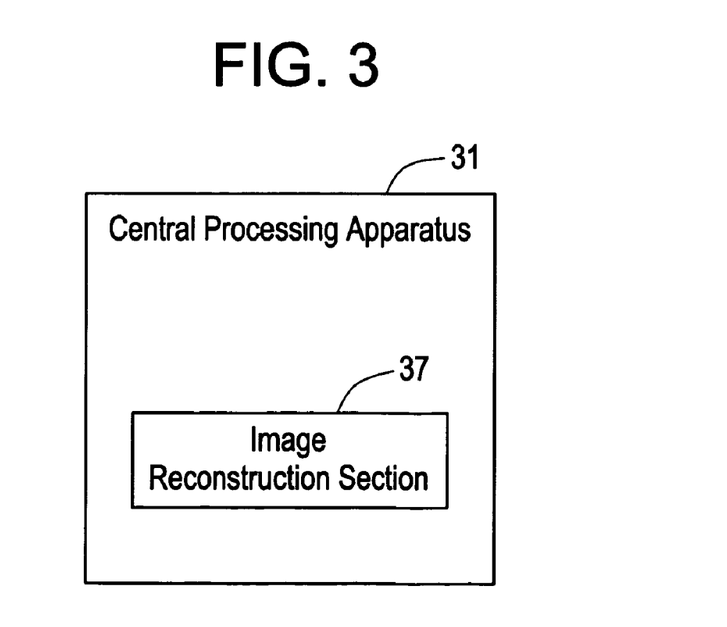
FIG. 3 is a block diagram schematically showing the central processing apparatus 31 in the X-ray CT apparatus 1 shown in FIG. 1.

FIG. 3 is a block diagram schematically showing an exemplary configuration of the central processing apparatus.

The central processing apparatus 31 comprises an image reconstruction section 37.

The image reconstruction section 37 is comprised of, for example, programs or the like. The image reconstruction section 37 is supplied with data collected at the data collecting section 24 via a data collection buffer (not shown), and the section 37 uses the collected projection data to conduct image reconstruction. One embodiment of the reconstruction means of the present invention is represented by the image reconstruction section 37.

Next, an operation of the X-ray CT apparatus 1 in accordance with the present invention will be described with reference to the accompanying drawings.

Figure 4:
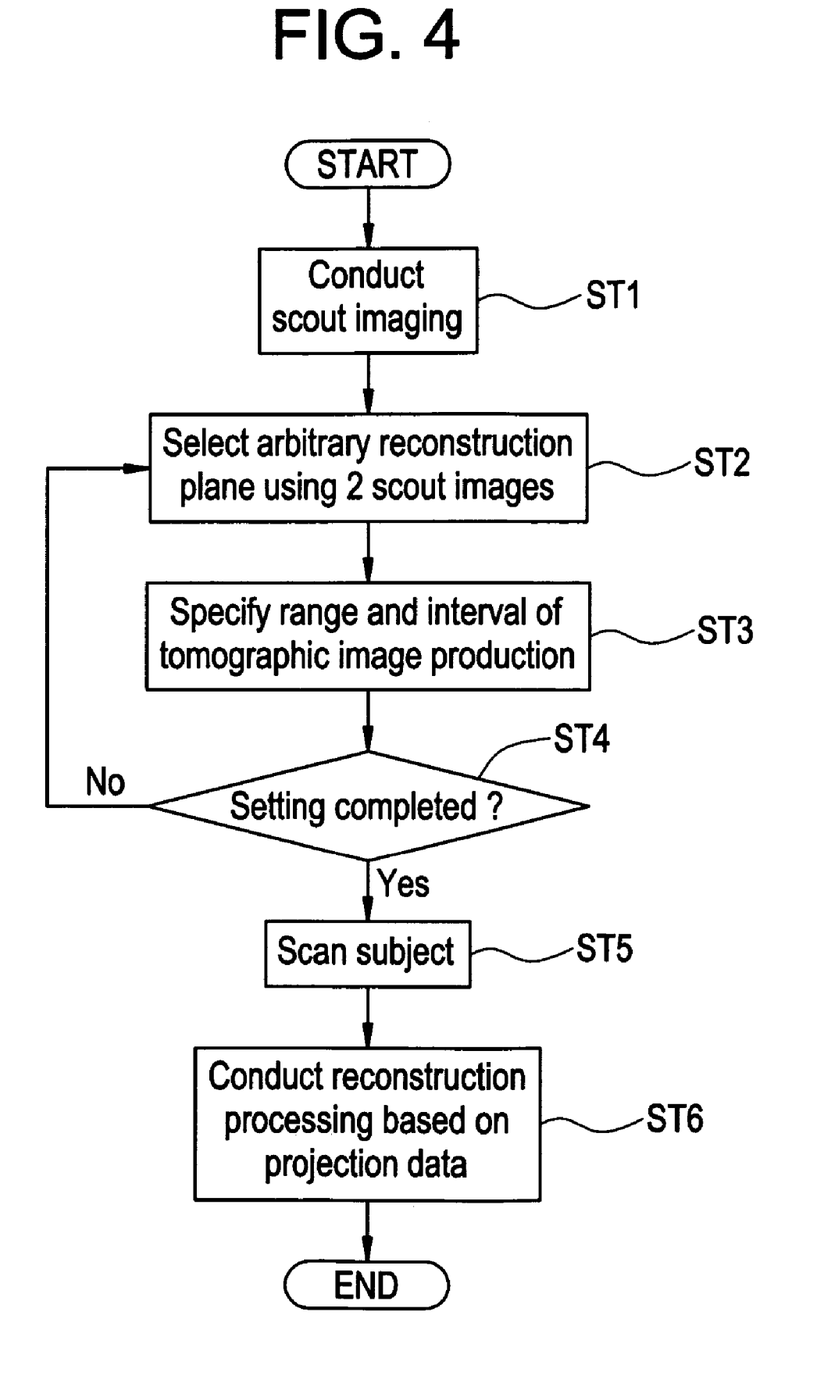
FIG. 4 is a flow chart explaining the operation of the X-ray CT apparatus 1 shown in FIG. 1.

FIG. 4 is a flow chart showing an operation of the X-ray CT apparatus 1 of the present invention. The imaging method of the present invention is executed using the X-ray CT apparatus 1 of the present invention.

The user first uses the input device 32 to specify a direction and a range for scout imaging, and scout imaging is conducted based on the specified range (ST1). The scout imaging is conducted in at least two directions. In the present embodiment, for example, scout images in sagittal and coronal planes of the subject are produced.

The central processing apparatus 31 controls the scan gantry 2 to scan the subject in a range and a direction based on the specified conditions. At that time, the scan gantry 2 conducts the scan while translating and without rotating, with the X-ray tube 21 and detector array 23 kept at a constant position. The detector array 23 outputs obtained data to the central processing apparatus 31 via the data collecting section 24. The central processing apparatus 31 produces a scout image based on the obtained data, and outputs the image to the display device 33.

Next, the user observes the scout image of the subject displayed on the display device 33, and selects an arbitrary reconstruction plane using the two scout images (ST2).

Figure 5A:
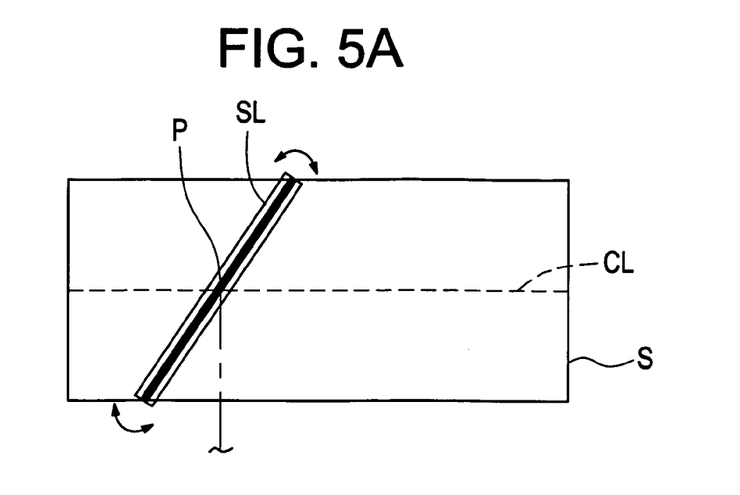
FIGS. 5a, 5b, and 5c are schematic diagrams showing part of the step of defining a reconstruction plane in the X-ray CT apparatus 1 shown in FIG. 1.
Figure 5B:
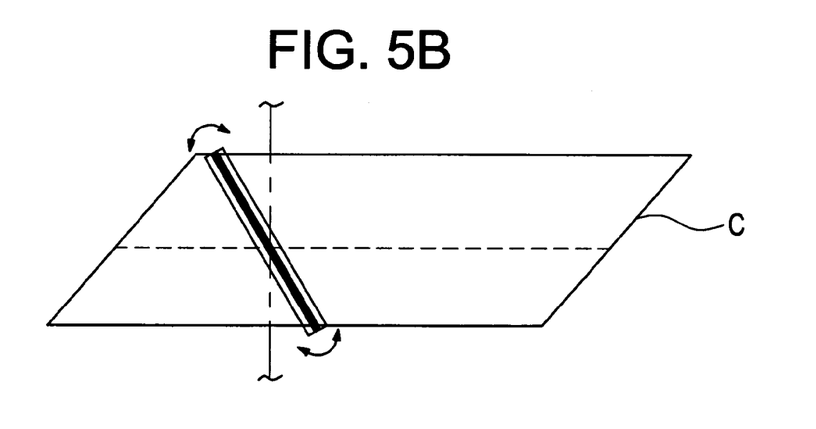

FIG. 5(a) is a schematic diagram showing the step of setting a straight line SL forming an arbitrary angle with respect to a line of intersection CL on a sagittal plane S; FIG. 5(b) is a schematic diagram showing the step of setting a straight line SL forming an arbitrary angle with respect to the line of intersection CL on a coronal plane C; and FIG. 5(c) is a schematic diagram showing the step of selecting a reconstruction plane RP based on the straight line SL.

As shown in FIG. 5(a), the user first defines a reference position P on the line of intersection CL between the sagittal plane S and coronal plane C on the scout image in the sagittal plane S by an operation of the reconstruction plane defining section 35 using a cursor or the like. Next, the user operates the reconstruction plane defining section 35 to set a straight line SL passing through the reference position P with reference to the scout image and the imaged region in the subject so that the line SL forms a certain angle with respect to the line of intersection CL. The user presses a set key or the like on the reconstruction plane defining section 35 to cause the central processing apparatus 31 to store the setting into the storage device 34.

Next, as shown in FIG. 5(b), the user similarly operates the reconstruction plane defining section 35 in the scout image in the coronal plane C, and sets a straight line SL passing through the reference position P so that the line SL forms a certain angle with respect to the line of intersection CL. At that time, the central processing apparatus 31 transposes the reference position P on the line of intersection CL defined in the scout image in the sagittal plane S to the scout image in the coronal plane C. Again, the user presses a set key or the like on the reconstruction plane defining section 35 to cause the central processing apparatus 31 to store the setting into the storage device 34.

Figure 5C:
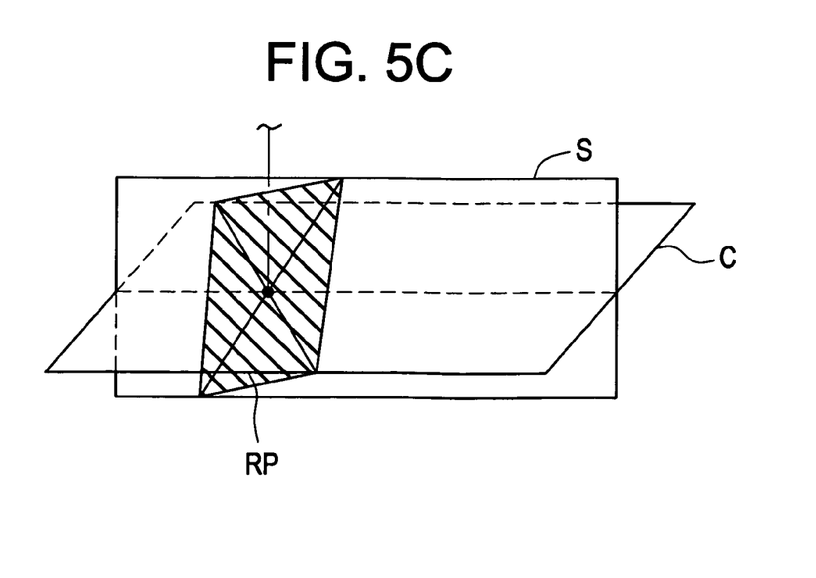

Next, as shown in FIG. 5(c), the central processing apparatus 31 displays a reconstruction plane RP selected by the straight lines SL set in the scout images in the sagittal plane S and coronal plane C on the display device 33. The user views the displayed image and makes confirmation. It is possible to finely adjust the reconstruction plane RP as needed. The user can adjust the two straight lines for selecting the reconstruction plane RP displayed on the display device 33 by moving the lines by the operation of the reconstruction plane defining section 35 by the cursor or the like.

Next, the user specifies a range of images to be produced by reconstruction and an interval at which the images are to be produced (ST3).

Figure 6:
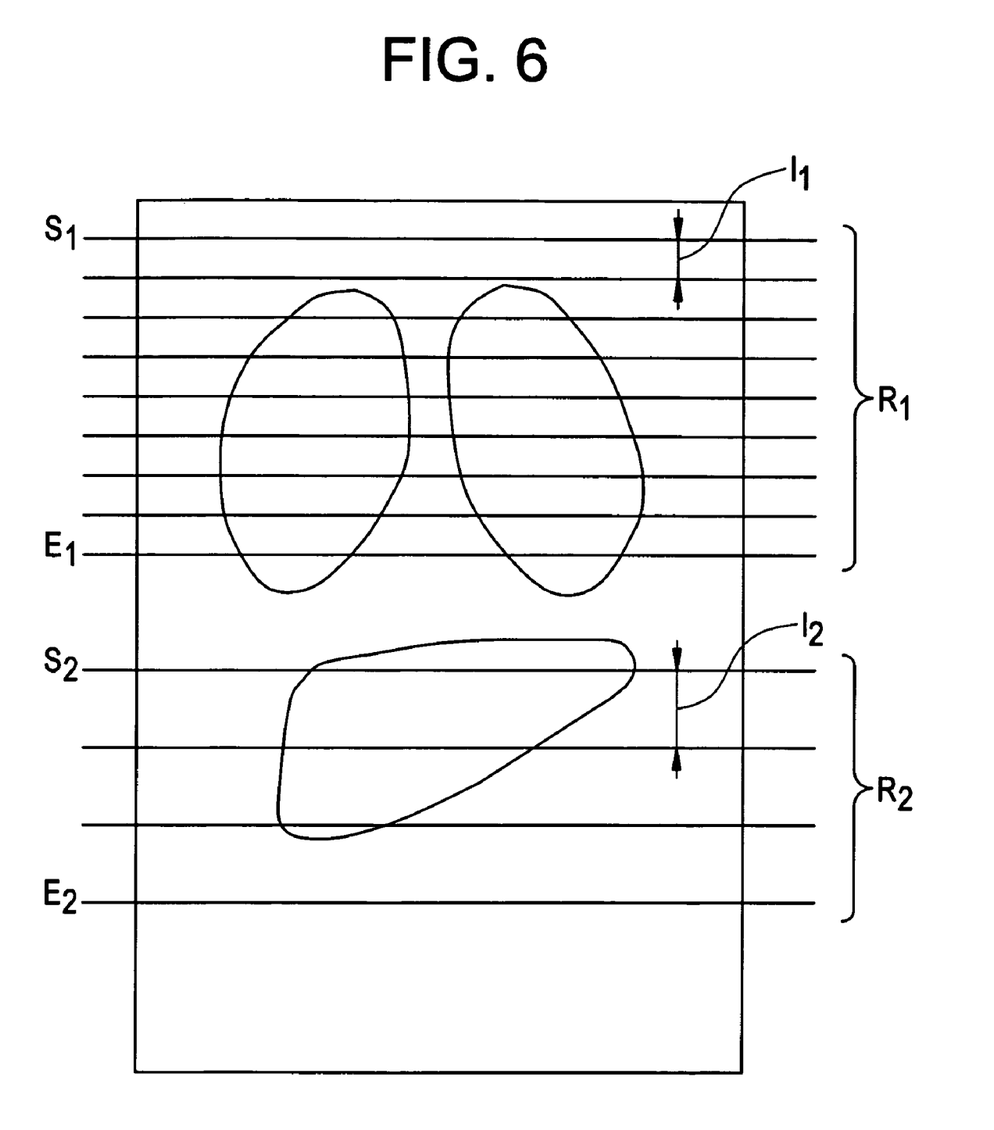
FIG. 6 is a schematic diagram showing part of the step of specifying scan conditions in the X-ray CT apparatus 1 shown in FIG. 1.

FIG. 6 is a schematic diagram generally showing part of the step of specifying a range of images and an image production interval.

The schematic diagram shown in FIG. 6 represents substantially the same tomographic image as that in the coronal plane, for example, shown in FIG. 5. As shown in FIG. 6, the user uses the reconstruction plane defining section 35 to specify a start position S1, an end position E1, and an image production interval I1 for producing images in a first region R1, on the display device 33. Moreover, a scan speed, a slice thickness for the images to be produced, a helical pitch and the like may be specified as well by an operation of the operating section 36 by the user.

Moreover, different image production intervals may be specified in one scan. In this case, following the specification for the first region R1, the user similarly specifies a start position S2, an end position E2, and an image production interval I2 for producing images in a second region R2, on the display device 33 via the reconstruction plane defining section 35.

The image production intervals I1 and I2 are differently specified between the first and second regions R1 and R2. Moreover, the reconstruction planes specified in the first and second regions R1 and R2 may be specified as non-parallel between the regions R1 and R2, for example. At that time, the user specifies the reconstruction planes in the second region R2 by executing Step ST2 described above.

Furthermore, the user may specify different scan speeds between the first and second regions R1 and R2 via the operating section 36. In this case, the central processing apparatus 31 conducts control to linearly change the speed in a range from the end position E1 of the first region R1 to the start position S2 of the second region R2.

The specifications are set by the user operating the input device 32 while observing the image displayed on the display device 33, and are stored in the storage device 34 via the central processing apparatus 31.

One embodiment of the step of defining a reconstruction plane of the present invention is represented by Steps ST1–ST3.

Next, the selected reconstruction planes, reconstruction conditions and scan conditions are confirmed, and if necessary, the process from Step ST2 is redone (ST4).

Alternatively, since the reconstruction planes are defined in parallel between the first and second regions R1 and R2 in the case described above, the user may select reconstruction planes in another region in a direction different from that specified in the first and second regions R1 and R2.

Once the reconstruction planes, reconstruction conditions and scan conditions have been established, the central processing apparatus 31 selects cone beam scan conditions such as a helical pitch based on the image production interval and imaged region, and displays them on the display device 33. These scan conditions are preset by a program or the like stored in the storage device 34 as default conditions. The user modifies the displayed scan conditions via the input device 32 as needed. The central processing apparatus 31 stores the modified scan conditions into the storage device 34.

Moreover, the central processing apparatus 31 defines cone beam reconstruction conditions based on the specified reconstruction planes, image production interval and slice thickness. Specifically, the central processing apparatus 31 sets address data of the detector array 23 detected in a certain frame to be used in reconstruction of a certain region in the reconstruction plane. The setting of the reconstruction conditions as described above may be conducted after Step ST5 which will be described next.

After defining the reconstruction planes, reconstruction conditions and scan conditions, the subject is scanned based on the defined conditions (ST5).

The central processing apparatus 31 sends a command to the scan gantry 2 and imaging table 4 based on a program on the storage device 34 supplemented with the aforementioned modifications. Consequently, the scan gantry 2 scans the subject placed at a predefined position from the scan start position to the scan end position based on the specified scan speed. The detector array 23 outputs detected projection data to the central processing apparatus 31 via the data collecting section 24. The central processing apparatus 31 stores the input data into the storage device 34. One embodiment of the step of scanning of the present invention is represented by Step ST5.

Next, the central processing apparatus 31 conducts reconstruction processing based on the projection data obtained at Step ST5 and the conditions defined at Steps ST2 and ST3 (ST6).

The central processing apparatus 31 conducts reconstruction processing based on a program such as an existing cone beam reconstruction program stored in the storage device 34. The central processing apparatus 31 displays a tomographic image in the selected reconstruction plane on the display device 33. Consequently, the user can observe a preselected reconstruction plane in a specified region. One embodiment of the step of reconstructing of the present invention is represented by Step ST6.

According to the imaging method of the present invention, by conducting a scan on a subject using cone-shaped X-rays and cone beam reconstruction, a reconstruction plane can be unrestrictedly defined in a three-dimensional manner without depending upon the emission angle or direction of emitted X-rays, the direction of X-ray detector arrangement, or the direction of rotation of the scan gantry.

Moreover, since the interval at which reconstruction planes are produced, etc., is variable among a plurality of regions, a scan having a varying speed can be conducted in a helical scan, for example. Furthermore, since a reconstruction plane is defined before a scan, a tomographic image in an arbitrary plane can be obtained without producing an axial image. In addition, reconstruction planes may be defined as non-parallel between the regions.

According to the X-ray CT apparatus of the present invention, by conducting a scan on a subject using cone-shaped X-rays and cone beam reconstruction, a reconstruction plane can be unrestrictedly defined in a three-dimensional manner without depending upon the emission angle or direction of emitted X-rays, the direction of X-ray detector arrangement, or the direction of rotation of the scan gantry.

Moreover, by separately selecting the angle of straight lines defined on a scout image on a display device before a scan, a reconstruction plane can be specified in a visually simple manner. Furthermore, in addition to the interval at which reconstruction planes are produced, it is possible to specify the slice thickness on the display screen, and therefore, existence of an overlap of images can be visually confirmed.

The imaging apparatus of the present invention is not limited to the aforementioned embodiment.

For example, the reconstruction planes defined at Step ST3 in the first and second regions shown in FIG. 6 may be parallel. In this case, setting of a reconstruction plane in the second region may be omitted. Moreover, while scout images are captured in the sagittal and coronal planes, the imaging plane for a scout image is not particularly limited.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT apparatus having an X-ray source and an X-ray detector disposed to face said X-ray source with a subject placed therebetween, for rotating at least one of said X-ray source and said X-ray detector around said subject and detecting cone-shaped X-rays emitted from said X-ray source toward said subject by said X-ray detector, comprising:
a defining device for defining a reconstruction plane for said subject in a plane non-parallel to a lane formed by rotation of at least one of said X-ray source and said X-ray detector around said subject, wherein said defining device defines an arbitrary reconstruction plane using a scout image parallel to a direction of a body axis connecting a head to toes of said subject.

2. The X-ray CT apparatus of claim 1, wherein:
said defining device defines an interval between adjacent reconstruction planes.

3. The X-ray CT apparatus of claim 1, further comprising:
a reconstruction device for cone-beam reconstructing a tomographic image of said subject in said reconstruction plane defined by said defining device, using projection data detected by said X-ray detector.

4. The X-ray CT apparatus of claim 1, wherein:
said defining device defines a reference position on a line of intersection of a plurality of said scout images to define said reconstruction plane passing through said reference position.

5. The X-ray CT apparatus of claim 4, wherein:
said defining device defines, in each scout image, a straight line passing through said reference position forming an arbitrary angle with respect to said line of intersection, and defines said reconstruction plane by two said straight lines intersecting at said reference position.

6. The X-ray CT apparatus of claim 1, wherein:
said defining device defines a start position and an end position for producing said reconstruction plane, and a scan speed between said start and end positions.

7. The X-ray CT apparatus of claim 6, wherein:
said defining device defines a plurality of regions in which said reconstruction planes are produced, confined by said start and end positions.

8. The X-ray CT apparatus of claim 7, wherein:
said defining device defines said reconstruction plane as non-parallel between the defined regions.

9. The X-ray CT apparatus of claim 7, wherein:
said defining device defines said interval between adjacent reconstruction planes as different between the defined regions.

10. The X-ray CT apparatus of claim 6, wherein:
said defining device defines a plurality of regions in which said reconstruction planes are produced, confined by said start and end positions, and defines said scan speed different between the defined regions.

11. The X-ray CT apparatus of claim 7, wherein:
said defining device defines the plurality of defined regions as consecutive regions.

12. The X-ray CT apparatus of claim 7, wherein:
said defining device defines a slice thickness of said reconstruction plane as different between the defined regions.

13. An imaging method for an X-ray CT apparatus having an X-ray source and an X-ray detector disposed to face said X-ray source with a subject placed therebetween, for rotating at least one of said X-ray source and said X-ray detector around said subject and detecting X-rays emitted from said X-ray source toward said subject by said X-ray detector, comprising the steps of:
defining a reconstruction plane for said subject in a plane non-parallel to a plane formed by rotation of at least one of said X-ray source and said X-ray detector around said subject said step of defining a reconstruction plane comprises the steps of
producing a scout image parallel to a direction of a body axis connecting a head to toes of said subject placed at a predefined position;
selecting an arbitrary reconstruction plane using said scout image; and
defining an interval between adjacent reconstruction planes;
scanning said subject while emitting cone-shaped X-rays from said X-ray source; and
reconstructing a tomographic image of said subject based on said defined reconstruction plane.

14. The imaging method of claim 13, wherein:
said step of producing a scout image produces said scout image in at least two different directions; and
said step of selecting a reconstruction plane defines a reference position on a line of intersection of a plurality of said scout images to define said reconstruction plane passing through said reference position.

15. The imaging method of claim 14, wherein:
said step of selecting a reconstruction plane defines, in each scout image, a straight line passing through said reference position forming an arbitrary angle with respect to said line of intersection, and defines said reconstruction plane as a plane determined by two said straight lines intersecting at said reference position.

16. The imaging method of claim 13, wherein:
said step of selecting a reconstruction plane defines a start position and an end position for producing said reconstruction plane, and a scan speed between said start and end positions.

17. The imaging method of claim 16, wherein:
said step of selecting a reconstruction plane defines a plurality of regions in which said reconstruction planes are produced, confined by said start and end positions.

18. The imaging method of claim 17, wherein:
said step of selecting a reconstruction plane defines said reconstruction plane as non-parallel between the defined regions.

* * * * *

UNITED STATES PATENT AND TRADEMARK OFFICE
CERTIFICATE OF CORRECTION

PATENT NO. : 7,164,746 B2
APPLICATION NO. : 11/032559
DATED : January 16, 2007
INVENTOR(S) : Gohno et al.

It is certified that error appears in the above-identified patent and that said Letters Patent is hereby corrected as shown below:

In Claim 1, column 8, line 16, delete "lane" and insert therefor -- plane --.

In Claim 13, column 9, line 15, delete "subject said" and insert therefor -- subject, said --.

Signed and Sealed this

Tenth Day of June, 2008

JON W. DUDAS
*Director of the United States Patent and Trademark Office*